(12) United States Patent
Jeffrey

(10) Patent No.: US 6,811,548 B2
(45) Date of Patent: Nov. 2, 2004

(54) MATERIALS DELIVERY DEVICE

(76) Inventor: Peter Jeffrey, 28 Riverbank Rd., Liverpool L19 9DH (GB)

( * ) Notice: Subject to any disclaimer, the term of this patent is extended or adjusted under 35 U.S.C. 154(b) by 0 days.

(21) Appl. No.: 09/155,812

(22) PCT Filed: Apr. 1, 1997

(86) PCT No.: PCT/GB97/00905
§ 371 (c)(1),
(2), (4) Date: Sep. 30, 1998

(87) PCT Pub. No.: WO97/36623
PCT Pub. Date: Oct. 9, 1997

(65) Prior Publication Data
US 2002/0029018 A1 Mar. 7, 2002

(30) Foreign Application Priority Data
Mar. 30, 1996 (GB) ............................................. 9606829

(51) Int. Cl.[7] ............................................... A61M 5/00
(52) U.S. Cl. ...................................... 604/207; 604/207
(58) Field of Search ........................ 604/207–211, 224, 604/218, 135, 131–134

(56) References Cited

U.S. PATENT DOCUMENTS

| | | | | |
|---|---|---|---|---|
| 4,668,220 A | * | 5/1987 | Hawrylenko | ................ 604/155 |
| 4,929,234 A | * | 5/1990 | Chen | ........................... 604/132 |
| 5,017,190 A | * | 5/1991 | Simon et al. | ............... 604/207 |
| 5,304,152 A | * | 4/1994 | Sams | .......................... 604/207 |
| 5,599,314 A | * | 2/1997 | Neill | ........................... 604/207 |
| 6,004,297 A | * | 12/1999 | Steenfeldt-Jensen et al. | ........................... 604/207 |
| 6,048,336 A | * | 4/2000 | Gabriel | ........................ 604/211 |

* cited by examiner

Primary Examiner—Brian L. Casler
Assistant Examiner—Kevin C. Sirmons
(74) Attorney, Agent, or Firm—Chapman and Cutler LLP

(57) ABSTRACT

Materials delivery devices, e.g. for drugs etc. (FIGS. 1–7) or body fluids (FIGS. 8–12), have administration means of piston-and-cylinder (100; 300) or peristaltic rollers and tube (546, 565; 646, 665; 746, 765; 846, 865; 946, 965) type, and intermittently incremental drive transmission means of cooperating toothed rack (143) or wheel (345, 445; 545; 645; 745; 845; 945) and deflectable biassed pawl (153, 156; 343, 356; 453, 456; 553, 556; 653, 656; 753, 756; 853, 856; 953, 956) type driven by pulsed reciprocating solenoid action (110; 310; 410; 510). Portable patient-wearable drug delivery devices (10; 30; 40; 50) can use pre-loaded cartridges (120; 320; 420; 520) and have solenoid drive (130) for needle-entry and battery-powered electronic control, etc. Intravenous infusion pumps (60; 70; 80; 90) can operate relative to body fluid reservoirs or for body fluid transfers.

28 Claims, 10 Drawing Sheets

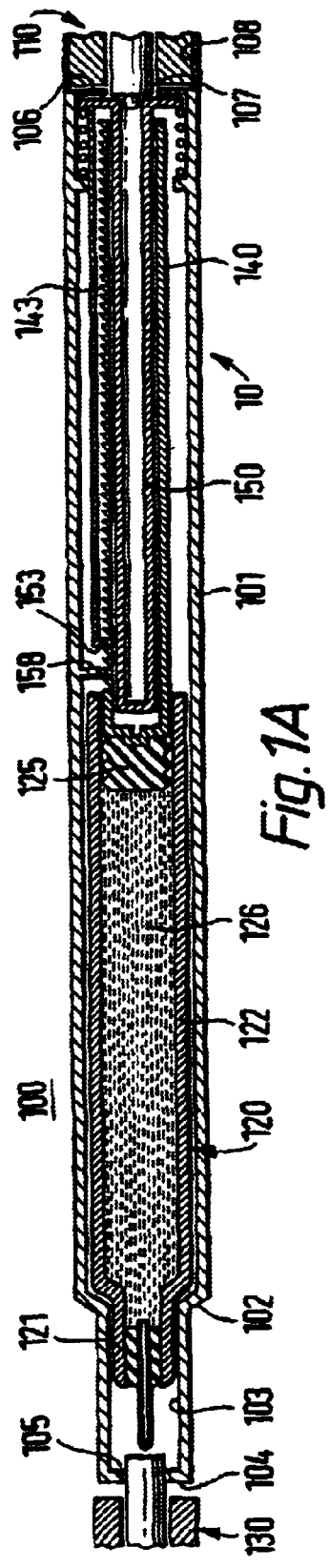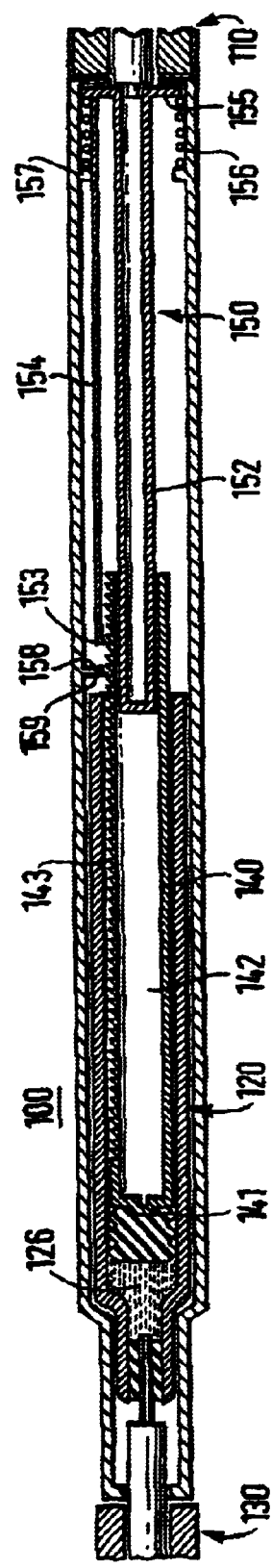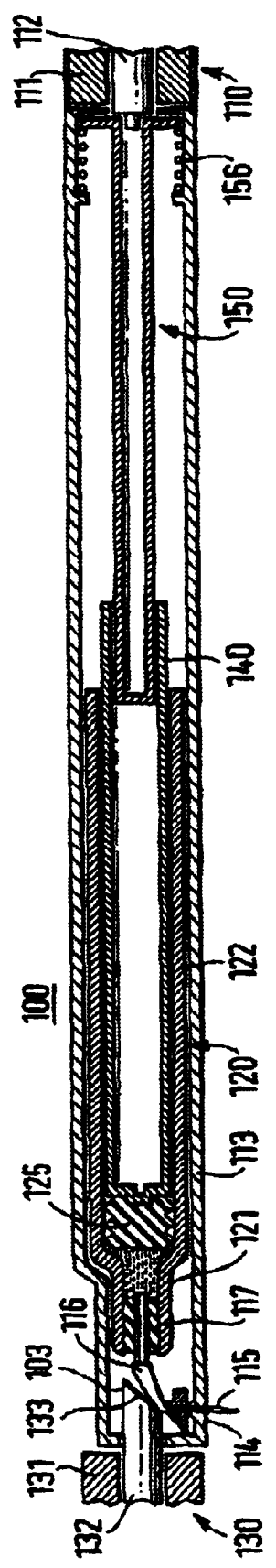

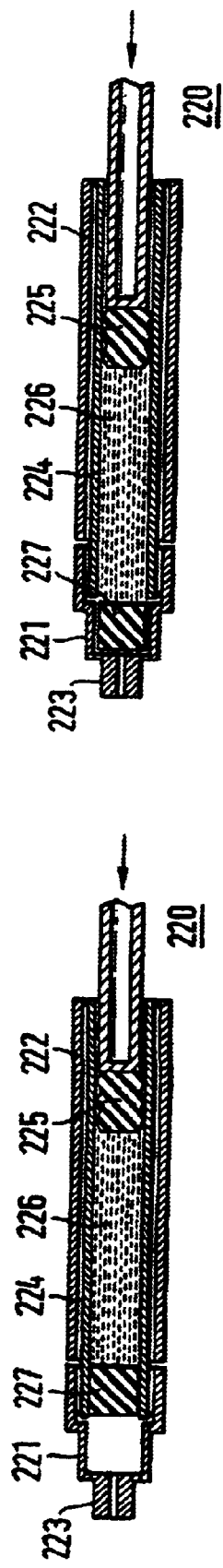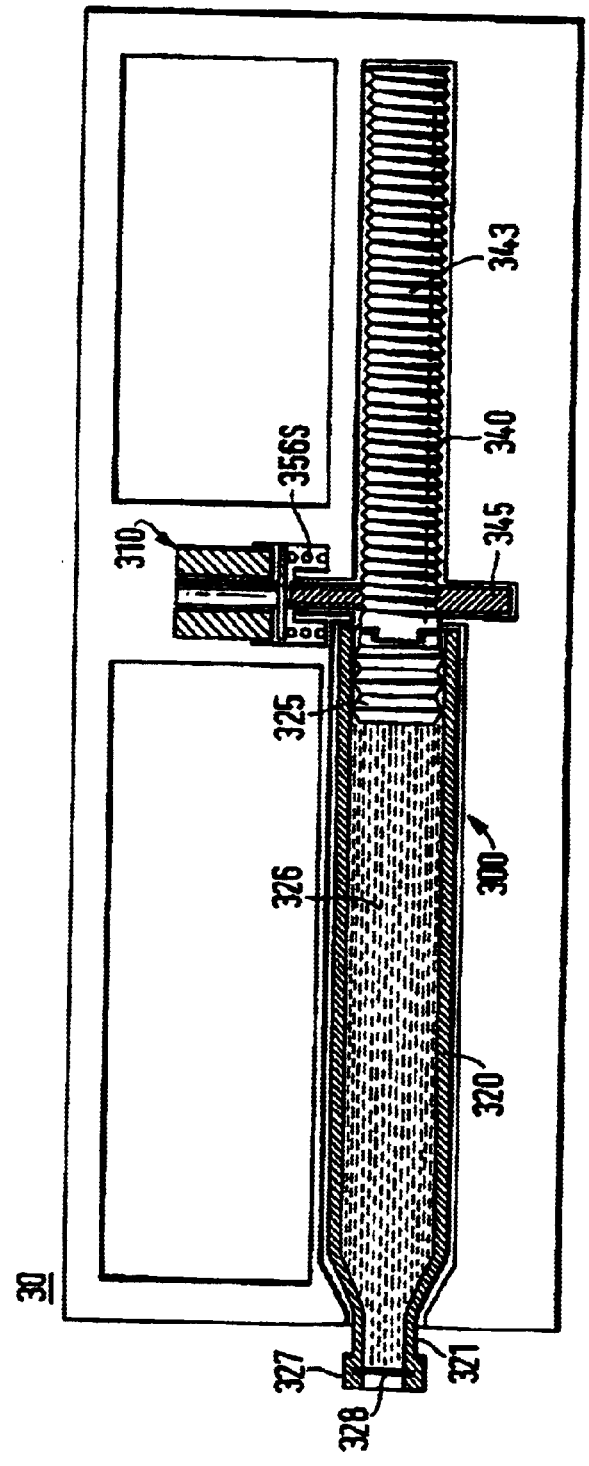

MATERIALS DELIVERY DEVICE

This invention relates to supplying or delivering flowable materials usually liquids but feasibly anything, such as pastes or gels or even dry comminuted forms, capable of progressive pressurised delivery, as by piston-and-cylinder or peristaltic pump action, including (though not limited to) accurately controlled delivery in or at low quantities or rates over extended periods of time.

This invention arises specifically in relation to parenteral administration of drugs etc to patients, where requirements can be for substantially continuing dosing with drugs etc, often at very low-dosage rates or levels and over long periods of time, or for such frequent dosing that consistent timely administration dose-by-dose can be problematic even by health-care professionals for hospitalised patients. Resort is generally made to so-called syringe on infusion pumps that are normally driven by precision-geared rotary electric motors closely controlled and monitored by complex microprocessor-based electronic systems. Alternative drive systems include gas pressure as from inflated balloons, typically involving drugs etc delivery through a very small metering hole requiring micro-filtering of drugs etc. Such known syringe or infusion pumps tend to be bulky and expensive, often costing hundreds even thousands of pounds sterling. Patients concerned are necessarily virtually incapacitated during such drugs etc administration, though often, in themselves, not otherwise much debilitated.

It is a specific object of one aspect of this invention to provide, for substantially continuous and/or long tern use by patients, parenteral drugs etc delivery systems with inherent reliability but more convenient to use and/or less expensive, further preferably including capability for embodiment in forms so portable as to be wearable with reasonable safety.

However, in pursuing practical development, many further embodiments with other potentially highly advantageous applications and uses have come into consideration.

According to this invention, there is provided a materials delivery device having administration means that is progressively operable in a step-wise manner by intermittently incremental drive transmission means. For drugs etc administration, increment sizes and intervals between them can correspond to patients' dosage requirements.

Preferred incremental drive transmission means is of ratchet-type. Intermittently driven toothed pawl means can serve for movement of toothed actuator means in a one-way and non-returnable incremental manner, usually one tooth pitch each time. The toothed pawl means may be reciprocable, conveniently driven one way and released automatically by biasing, say suitable spring means. The pawl means may move the actuator in its drive stroke, or on its return stroke, and will usually deflect for its stroke not driving the actuator means. Preferred toothed pawl means is linearly driven, conveniently repeatedly by simple linear solenoid means, though rotary solenoids are known and could be used.

In piston-and-cylinder type delivery devices, spurting may be mitigated by energy storage-and-release provision between the piston-rod and the piston it drives, or between two parts of the piston-rod, say a spring compressed by a solenoid-driven drive stroke of the pawl means and expanding to drive the piston; and can further have an electric switch operative after energy release corresponding to full stroke piston movement. Another useful provision is ratchet latching means preventing any backward movement beyond increments of the actuator means, say a one-way deflecting latch arm or tooth, which can advantageously have associated even incorporated signalling means, for example including a piezoelectric device.

Such signalling means and switch provisions facilitate highly advantageous control and monitoring of each solenoid-driven delivery increment in terms of adequacy of movement of the actuator means represented by signalling means output for one full tooth deflection and return of the latch means and one full piston delivery stroke represented by switch operation neither too quickly nor too slowly; say as consecutive possible disables in an allowed delay period for an alarm state primed by each solenoid drive pulse. Desired setting up for regular pulses causing solenoid-driven incremental administrations is readily subject to augmenting by on-demand action to generate an additional solenoid drive pulse.

Suitable toothed actuator means can be a linear track of teeth provided on or directly associated with a drive rod of an administration piston, or be an intermediary toothed wheel, whether of simple or complex type, including gearing down via a lesser ring of teeth in rack-and-pinion relation with toothed piston drive rod means, or operative via threading in lead-screw relation with threaded piston drive-rod means. Up to many hundreds, indeed thousands, of increments can be provided in these ways in highly compact even user-wearable battery-powered devices.

Instead of operating delivery pistons of basically syringe-type delivery devices, whether or not for drugs etc administration, solenoid-operated toothed pawl means and ratchet-type drive transmission hereof may be applied to other delivery devices, including advantageously of a peristaltic nature, say where a toothed actuator wheel further carries or is in driving association with tube squeezing and supply metering roller means, such as an annular array of rollers also on or fixed to rotate as a whole array with the ratchet wheel and acting on the tube against support means, preferably biassed and tolerant of different tube sizes.

Advantageous parenteral drugs etc delivery devices of this invention using electric solenoid drive and ratchet-type incremental drive transmission are dramatically less expensive to produce for sale at much lower prices than presently available precision-geared rotary electric motor driven and microprocessor-controlled syringe or infusion pumps. Notably, preferred control and monitoring provisions can be much simpler, say switch and gate based relative to a clock source, and a counter, but still provide full monitoring and reliability of operation. Battery-powered compact units can be fully portable, even safely worn by users including in bed while sleeping, as will be described in detail.

A pre-loaded drugs etc cartridge may be used with its customary sealing and unloading piston operated by said piston-rod of piston-and-cylinder type delivery devices hereof. Alternatively, drugs etc contents may be drawn from a container, often also of pre-loaded type, perhaps particularly for peristaltic type delivery devices hereof. Other applications, for example in the food industry for metering various additives, may use either type of delivery device, including much larger than usual for drugs etc.

In one piston-and-cylinder embodiment of this invention, a holder for a pre-loaded cartridge complete with seal and dispensing piston may be cylindrical with the cartridge at a relatively forward position and the piston-rod relatively rearward in the holder alongside ratchet-drive transmission provisions. The piston-rod will be incrementally movable forwards in driving the piston along the cartridge. The pawl means will be reciprocable by intermittent operation of a rearward drive solenoid and bias-driven return. A hollow delivery needle from the cartridge can be selectively exposable at least for its pointed end. One suitable such needle provision has a medial bend or joint, such as at an angle to a deflectable tube, together with means for forcing its end out of the holder or extension thereof. Such forcing means may be operated by another solenoid at the forward end of the holder. This other solenoid action could be with a time delay for a prescribed number of first solenoid operations to fill the delivery needle before it is extended into the user. The whole may be mounted in a flattish carrier, including control and monitoring electronics and an electric battery, say mounted parallel with the holder in the carrier adapted to be worn by the user.

Other piston-and-cylinder embodiments of this invention can have other configurations and relationships, between their piston-rods, usually along with aligned drugs etc cartridges, and their ratchet-drive pawl means. Thus, a ratchet-wheel with larger and smaller rings of teeth, one (usually the smaller) in rack-and-pinion relation with piston-rod teeth, allows any angled/offset relationship, of which a parallel but offset relationship will be described in detail. For a ratchet-wheel in lead-screw relation with piston-rod threading, a transverse relationship is convenient between the directions of movement of the piston-rod and the reciprocal pawl mens.

Embodiments with peristaltic action, conveniently also using a ring-toothed ratchet-wheel but now with a concentric ring of tube-squeezing rollers can simply draw drugs etc (or any other suitably flowable material) from any container in any relative disposition, whether as a cartridge in the same enclosure or clipped thereto, or separate therefrom, or of some other nature, such as an intravenous (IV) drip-feed bag or whatever. Suitable squeezable peristaltic feed tubes can pass between the ratchet-wheel rollers and pressure-plate means as the support means, preferably biassed towards the rollers, say with a recess to increase length of its engagement by squeezing rollers.

Alternatively, the ring of rollers may be within a U-shaped constraining wall with the peristaltic tube passing between the rollers and the wall, say from connections at and through an end wall. Generally, in addition to varying ratchet drive or tooth/radius parameters, peristaltic-type devices hereof allow variation of capacity and performance simply by a range of different tube diameters. Moreover, a peristaltic embodiment having two similar tubes is capable of highly accurate fluid transfer, particularly operated by the same tube-squeezing rollers, as in taking out and returning body fluids (such as blood) in relation to out-of-body treatments.

Specific implementation of this invention, in various exemplary embodiments, will now be described in more detail with reference to the accompanying drawings in which:

FIGS. 1A, B, C are longitudinal sectional views of one compact piston-and-cylinder drugs etc delivery provision in ready-to-use, in-use, and empty states, respectively;

FIGS. 2A, B; C, D; E, F show more details of needle deflection, preferred energy storage-and-release, and ratchet-latching provisions, respectively;

FIGS. 3A, B, C, D are one part-longitudinal sectional, and three cross-sectional views on arrows B, C and D of a complete portable and user-wearable administration device;

FIG. 4 is an outline diagram for control and monitoring electronics;

FIGS. 5A, B show priming for another (known) type of pre-loaded drugs etc cartridge;

FIGS. 6A, B are part-longitudinal sectional and cross-sectional views of another compact piston-and-cylinder drugs etc administration device;

Figure 2B:
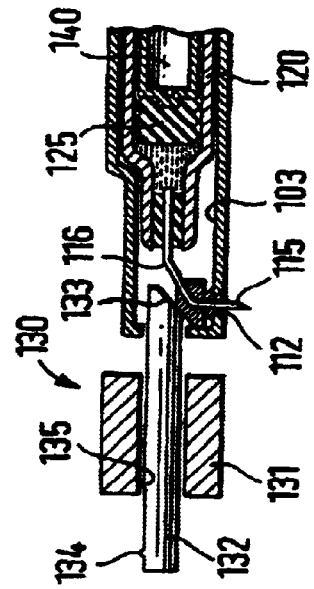
Figure 2A:
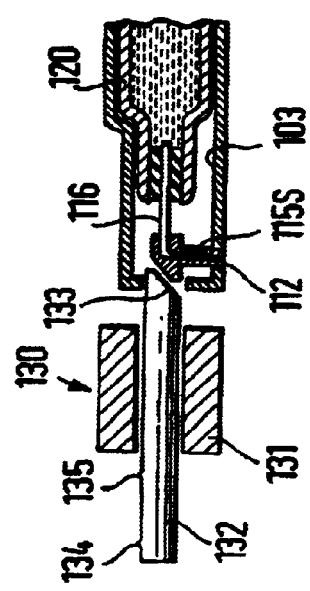
Figure 2D:
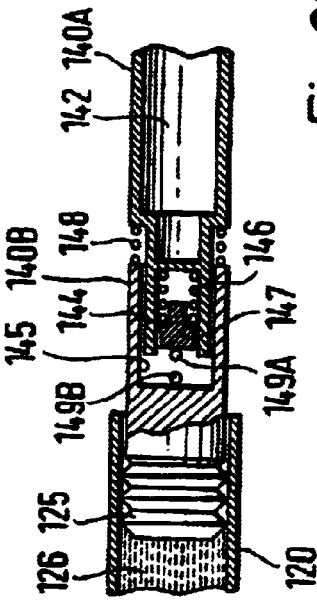

FIGS. 12A–D shows a dual-flow peristaltic device for fluid transfer purposes.

Referring first to FIGS. 1 to 4, in the interests of clarity, references 105–108, 121–126 appear mainly in FIG. 1A, references 111–116 mainly in FIG. 1C, and references 141–143, 151–159 mainly in FIG. 1B. Compact user-wearable device 10 includes a drugs etc dispenser 100 of generally elongate hollow cylindrical form. A generally D-section holder body 101 is necked down at 102 (except for its flat base face) to a projecting forward chamber 103 further returned at 104 to an aperture 105, and has a rearward annular partition 106 with an aperture 107 to an end chamber 108 for a linear solenoid 110 having a fixed coil 111 and reciprocably movable core 112. The unreduced base wall part 113 (see FIG. 1C taken at right angles to FIGS. 1A, B) of the forward chamber 103 has a side aperture 114 for deflection through it of a needle 115 shown connected at an angle to a tube 116 from a hub 117 of a pre-loaded drugs etc cartridge 120. The hub 117 is in an all-round reduced throat part 121 of the cartridge 120 from its main drugs etc dose-containing part 122 that is sealed off by a piston 125 capable of being forced down the main part 122 to unload the drugs etc contents 126.

A second linear solenoid 130 is shown at the reduced forward end of the holder body 100. Its coil 131 serves when energised to move its core 132 towards the needle 115 and tube 116. The core 132 projects through the forward body aperture 105 to a chamfered end 133 for deflection of the needle 115 out of the body side aperture 112, in which position the core 132 can be arranged to latch until positively moved into preferably also latched retracted state by opposite energisation of the solenoid coil 131 for needle retraction by resilience of the tube 116, or a bias spring, see latching bumps 134/5 in FIGS. 2A, B.

Other outlet provisions are feasible, not involving an extensible needle, e.g. a tube to a separate needle and/or transdermal patch.

Movement of the piston 125 is driven by piston-rod 140 suitably end-shaped at 141 for piston engagement and hollow at 142 to take a blind tubular guide part 152 of a pawl-carrier 150. The piston-rod 140 has a lengthwise row or rack of ratchet-tooth 143 to cooperate with pawl 153 on arm 154 extending from end-flanging 155 of the pawl carrier 150.

Figure 2C:
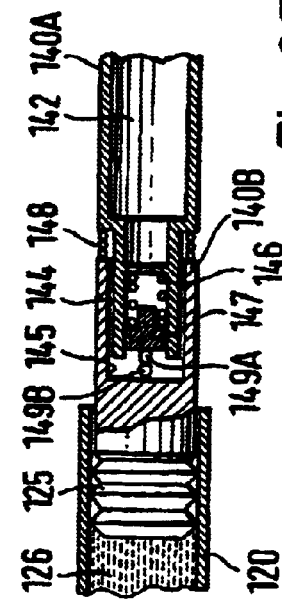
Figure 2F:
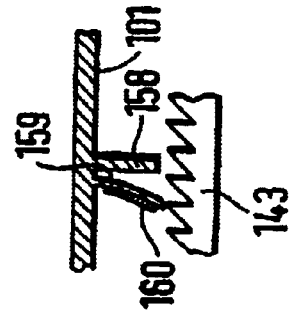
Figure 2E:
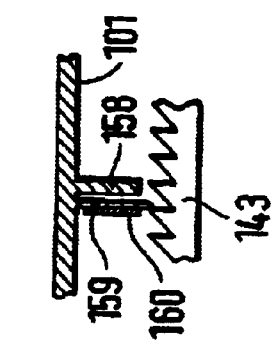
Figure 3A:
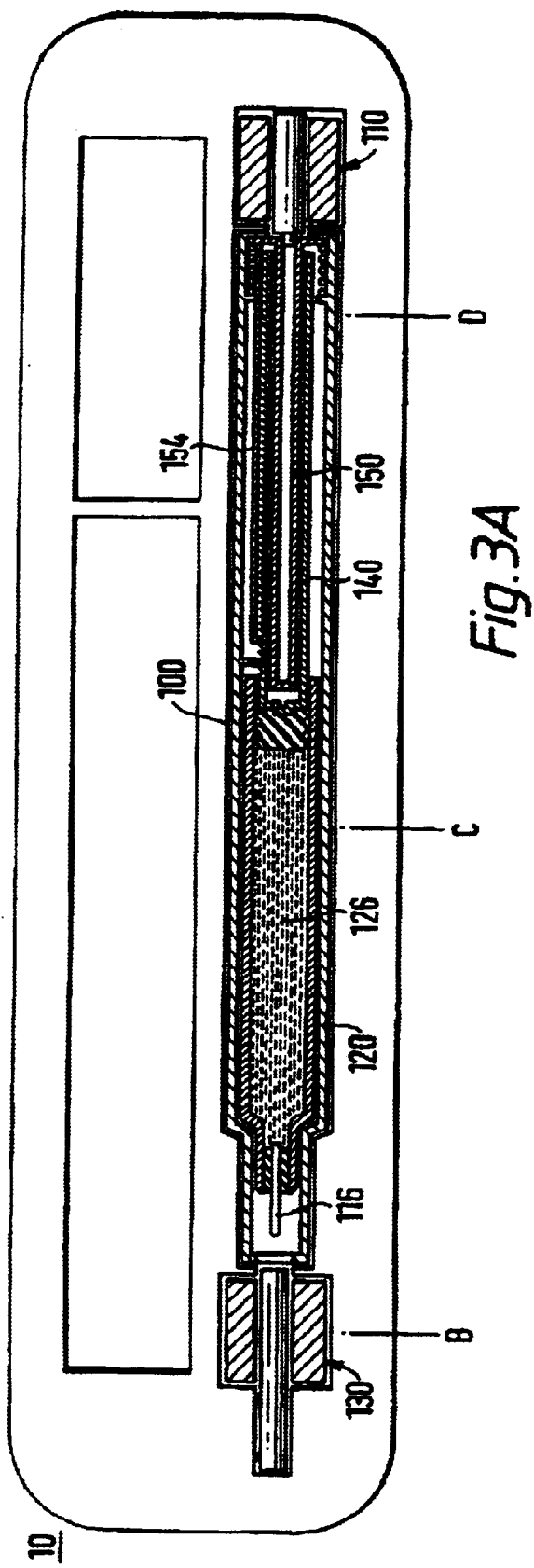
Figure 3B:
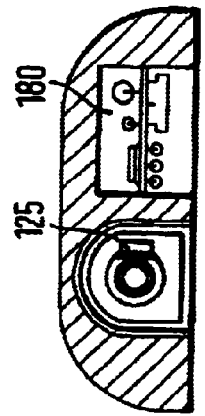
Figure 3C:
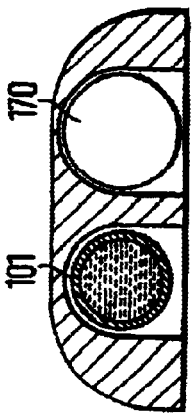
Figure 3D:
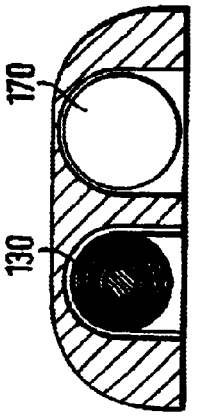

A preferred piston-rod is shown in FIGS. 2C, D as being of two-part form of which part 140A has the internal space 142 for the pawl carrier guide part 152 and will have the external ratchet teeth 143, and part 140B engages the cartridge piston 125. Tubular extension 144 of the part 140A is telescopic in recess 145 of the part 140B and houses a contact-biassing spring 146 for a switch contact carrier 147 suitably captive therein. An energy-storage-and-release spring 148 about the extension 144 acts between the parts 140A, B. Switch contacts 149A, B on the carrier 147 and base of the recess 145 make contact only when the spring 148 is compressed. Relatively sharp movement of the part 140A can thus be translated into slower corresponding movement of the part 140B with the switch contacts closing immediately but opening again at completion of movement of the part 140B.

The flanging 155 of the pawl carrier 150 is also shown acted upon by a return spring 156 acting from an abutment ring 157 of or suitably fixed in the holder body 101. Further abutment means (not shown) can be provided inside the holder body 101 adjacent the pawl-arm 154 to aid controlling its deflection in operation to be described. Another abutment 158 within the holder body serves to control one-way flexing of a latching member 159 for the ratchet-teeth 143. The latching member 151 can carry a piezoelectric flexure sensor 160 (see FIGS. 2E, F) for successive pulse signalling of each advance of the piston-rod 140 by a complete tooth of the ratchet 143.

The core 112 of the solenoid 110 engages the pawl carrier 150 in each drive pulse energisation of the coil 111, and drives the pawl carrier 150 with its pawl 153 by at least one pitch of the ratchet teeth 143. The piston-rod 150 is correspondingly moved and latched at 158/9. The pawl carrier 150 is returned by the spring 156 at the end of each energisation pulse for the solenoid coil 111. At least the preferred two-part piston-rod 140A, B of FIGS. 2C, D allows positive tolerance on ratchet action up to almost a second tooth pitch of movement without affecting accuracy of movement of the cartridge piston 125 by precisely one tooth pitch for each energisation of the solenoid 110. It is equally feasible, often advantageous, for the ratchet-drive action to be on return spring stroke of the pawl, e.g. with the return spring 156 acting between the partition 106 outward flanging of the pawl carrier 150 located corresponding to abutment 157, say on an all-round outer end-neck return and with the flanging 155 omitted.

The dispensing device 100 is shown in FIGS. 3A–D as enclosed within a flattish multi-compartment carrier 10 alongside a battery 170 and control electronics 180. The needle 115 will be extendible through the base of the carrier 10 and the whole may be worn by the user, say strapped in place and/or secured by adhesive.

Figure 4:
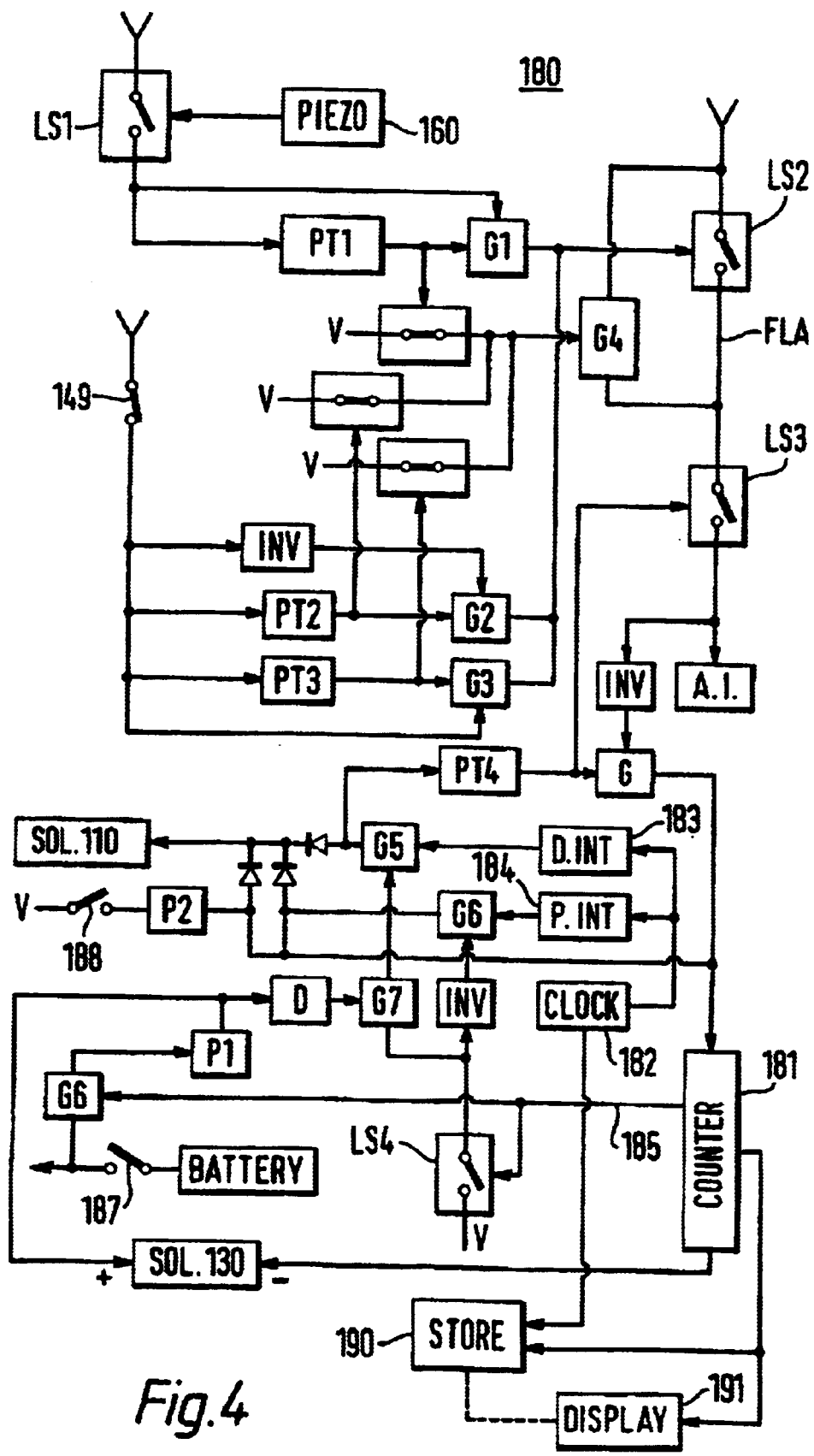

Control electronics 180, see FIG. 4, is much simpler than microprocessor-type precision-geared motor control hitherto. In operation, a counter 181 serves to count the number of incremental movements of the cartridge piston 125 corresponding to successful operations of the solenoid 110. Energisation pulses to the solenoid 110 come from a clock source 182, which may be a standard clock/watch quartz crystal chip, through dose-interval selection circuitry 183 set according to requirements of successive dosing of a patient, feasibly intendedly settable differently for each particular patient. Correct operation of the solenoid core 112 in advancing and latching of the piston-rod by one ratchet tooth (143) will produce two pulses from the piezoelectric device 160 shown controlling a latch switch LS1 of cycling ON/OFF type. The second such pulse (OFF for LS1) should be within a prescribed time interval of output from pulse timer PT1 so that gate G1 will not be enabled to operate normally-open alarm latch switch LS2. Correct drugs etc dose administration from the cartridge 120 through the needle 115 is represented by the ON (or closed) state of the normally-open contacts 149A,B ending after a minimum prescribed time interval of pulse timer PT2 (otherwise indicative of a leak due to improper tissue penetration) but before a maximum prescribed time interval of pulse timer PT3 (otherwise indicative of a blockage), so that neither of gates G2 and G3 will be enabled to operate the alarm latch switch LS2 in alarm indicator feed line FLA.

Another latch switch LS3 in series in the alarm feed line FLA can be provided to assure that a minimum time interval (of pulse timer PT4) elapses from each solenoid drive pulse before any operation of the alarm indicator AI, though this may not be considered essential. Also, positive monitoring of desired response of the piezoelectric device and the piston-rod 140 can be provided by way of outputs from the pulse timer PT1 and at least one of the pulse timers PT2 and PT3, all shown opening normally-closed switches NCS1, 2, 3 feeding gate G4 in a branch alarm feed line past the latch switch LS2.

The dose-interval setting means 183 supplies solenoid 110 and the pulse-interval timer 184 through gate G5 that is enabled only after an initialising phase involving priming the needle 115 by filling it with drugs etc and operating the solenoid 130 to extend the needle into tissue of the patient. Priming-interval setting means 184 can operate at a faster rate than dose-interval setting means 183 as there will be no tissue resistance to drugs etc flow, and its solenoid driving is controlled by gate G6 to be operative only until the counter 181 reaches a predetermined part-count assuring filling of the needle 115, see counter output 185, latching switch LS4 and inverter to the control input of the gate G6. At least this latching switch LS4 may tire out after a suitable period or be reset with the first dose-interval pulse. At the end of priming, part-count output 185 also opens gate G6 for pulse generator P to produce a positive drive pulse to the solenoid 130. Delay means D and gate G7 assure that the first dose-interval pulse can pass through gate G5 to the solenoid 110 only after a time interval sufficient for operation of the solenoid 130. A single operation of the start switch 187 assures all of the above operations.

The pulse timer PT2 and/or gate G2 can be disabled during priming if the priming pulse interval is so short that the alarm indicator will be operated, and that is not wanted. Alternatively, the alarm indicator input could be through another gate controlled by the part-count line 185. A manual over-ride, for extra on-demand dosing, is provided by switch 188 and pulse generator P2 directly to solenoid 110. Provision is readily made for limiting intervals or totals concerning additional dosing, as well as for battery state and/or malfunction monitoring. Illustrated diodes assure that the priming and any normal dose pulses are counted by the counter 181 but not applied to the dose-interval pulse timer PT4. Alternatively, the pulse timer PT4 could be disabled and/or by-passed.

A preset maximum count related to safely dispensable cartridge contents results in negative energisation of the solenoid 130 to retract the needle from the user's tissue. A display 190, usually of liquid-crystal type, for contents of the counter 181 is useful for calculating how many doses are left, even indicating that directly, and can readily be extended to show time(s) of initiation, last dose, next dose, number of additional doses, battery life left, etc. Store means 191 for keeping a record of doses and times of administration can be useful, including for monitoring additional manual doses, as well as for checking automatic operation. A permanent indicator for correct or incorrect functioning is preferred, say as or in the alarm indicator AI, such as a low power light-emitting diode (LED) to flash continuously during correct operation but to change colour or go continuous for any malfunction, or impending problem, such as low battery power.

As described and illustrated by FIG. 4, individual functions have been treated largely individually. There may be scope for sharing gates and pulse timers etc, and certainly for generally more efficient logic/switch usage, including of different types, all within the expertise of electronics engineers, including bespoke application to configurable semiconductor integrated circuitry, and expectedly more economically than for programmed microprocessors (though such can obviously be used if desired).

A larger count for priming will be required for the cartridge 220 of FIGS. 5A, B by reason of formation as an outer body 222 that is end-reduced 221 to a needle receptor 223 and an inner straight tube 224 for drugs etc contents 226 between a piston 225 and a similar plug 227 that needs to be driven out before drugs etc contents can be dispensed past it (see FIG. 5B) The piston-rod 240 will, of course, have ratchet teeth (not shown) and can be of two-part form (if not driven on return bias strokes).

Figure 6B:
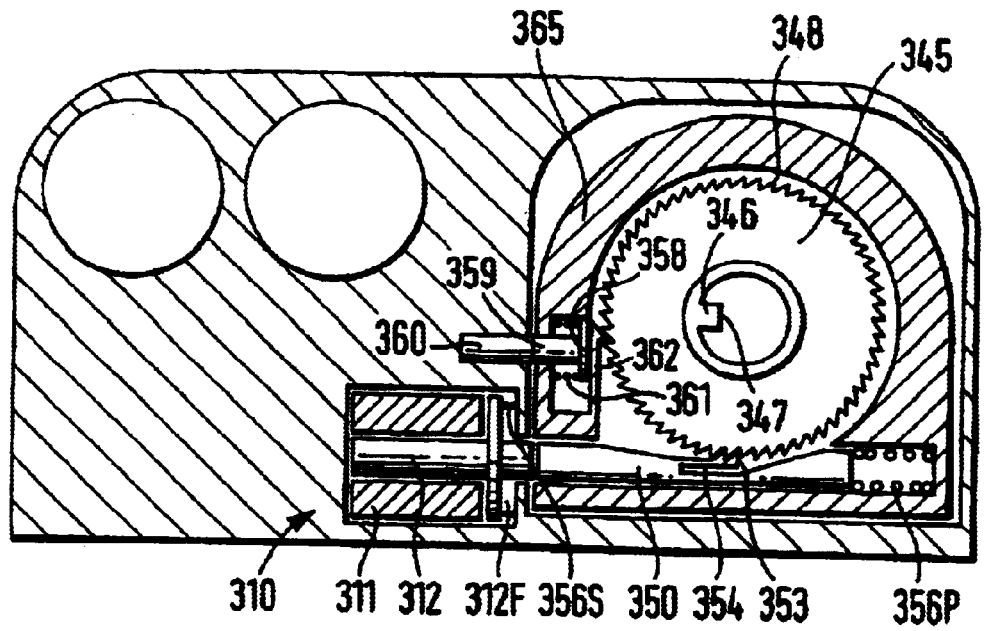

FIGS. 6A and 6B show a version with another example of feasible drugs etc cartridge 320 having a reduced end 321 and a needle-piercable or needle-less connector 327 with a septum seal disc 328. The piston-rod 340 is externally threaded at 343 (instead of having ratchet-teeth) and cooperates with an internally threaded nut or wheel 345 for lead-screw-type lengthwise incremental movement of the piston-rod 340 by virtue of anti-rotation key 346 and keyway 347. The drive nut or wheel 345 has ratchet teeth 348 about its rim and is driven by a tangentially acting pawl 353 on a deflectable arm 354 of a pawl carrier 350 reciprocably driven transversely of the piston-rod 340 by core 312 of solenoid 310 when its core 311 is pulsed. Separate return springs are shown at 356S and 356P for the solenoid core 312 and the pawl carrier 350, respectively, acting between a core flange 312F and a mount housing 365, and from end of a guide slot in the mount housing 365. Advantageous mount housing 365 is shown encircling the drive nut or wheel 345 and further accommodating a pawl-type latch 358 for the drive nut or wheel 345. Alternative tooth-by-tooth movement-sensing means is shown as a reciprocable flanged element 359 spring-loaded at 361 against deflectable latch-pawl arm 362 and with a transducer element 360 sensing tooth-by-tooth reciprocation. Twin batteries are shown in the battery compartment spaced from the electronics compartment by the ratchet wheel 345 and related incremental driving parts.

The highly compact pawl-carrier 350 is notably advantageous, and very simply applied to reversed action, i.e. with the spring-biassed stroke driving ratchet teeth, by sloping the ratchet and pawl teeth 343/353 oppositely to that shown, so that the pawl arm 354 deflects on the solenoid core drive stroke then hauls the ratchet tooth back—when, of course, no drive cushioning as in FIGS. 2C, D is required.

This embodiment of FIGS. 6A, B is capable of administering extremely small doses and/or a very large number of doses, for example 2,500 for a drive nut with 50 teeth and a piston-rod with 50 turns of thread. Again, however, a complete assembly in a multi-compartment carrier 30 is compact and capable of being worn by the user. Two teeth are shown for the pawl 353, but its action is essentially the same as described above.

Figure 7:
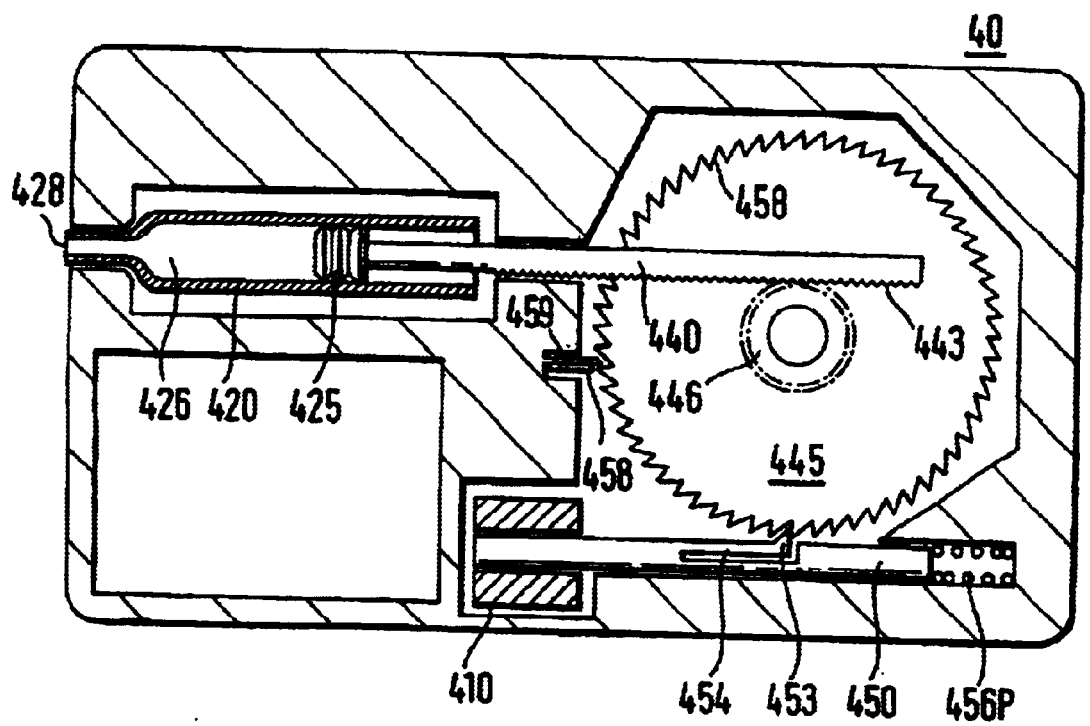
FIG. 7 is an outline view of a third compact piston-and-cylinder drugs etc administration device.

FIG. 7 has similar parts references with first digits advanced to "4", and shows an intermediate dosage embodiment with a similar arrangement of drive solenoid 410 and pawl carrier 450 with inset deflectable pawl arm 454 to pawl tooth 453, and drive nut or wheel 445 with ratchet teeth 458 about its outer rim. However, the piston-rod 440 has drive teeth 443 as for FIG. 1, and the drive nut or wheel 445 has another stepped ring of teeth 446 for rack-and-pinion type drive. The greater diameter of the drive nut or wheel 445 to its outer ratchet-teeth 453 readily permits either or both of enhanced practicality of pawl-and-ratchet teeth action for a similar number of teeth, and more and finer dosages for a larger number of ratchet teeth 453. The tooth-by-tooth movement sensor 459 and ratchet latch 458 are essentially as for FIG. 1.

Again, there is mounting in a multi-compartmented carrier 40, this time with substantial off-set of parallel rather than transverse piston-rod etc and pawl carrier movement. Also, a single corner-adjacent compartment is shown for battery and electronics accommodation.

As to dosing and device utility for drugs etc administration, it should he noted that inexpensive moulded piston-rods can have up to at least 500 accurate pawl-drivable teeth in a 50-millimeter length, and similar factors apply to rim- and step-toothed ratchet wheels. Thus, direct-drive straight ratchet embodiments (FIGS. 1 to 4) for 100 or many more doses, indirect-drive embodiments (FIG. 7) using dual-ring toothed ratchet wheels for 1,000 or many more doses, and screw thread using embodiments (FIGS. 6A, B) embodiments for 2,500 or many more doses represent enormously diverse capability.

Figure 8:
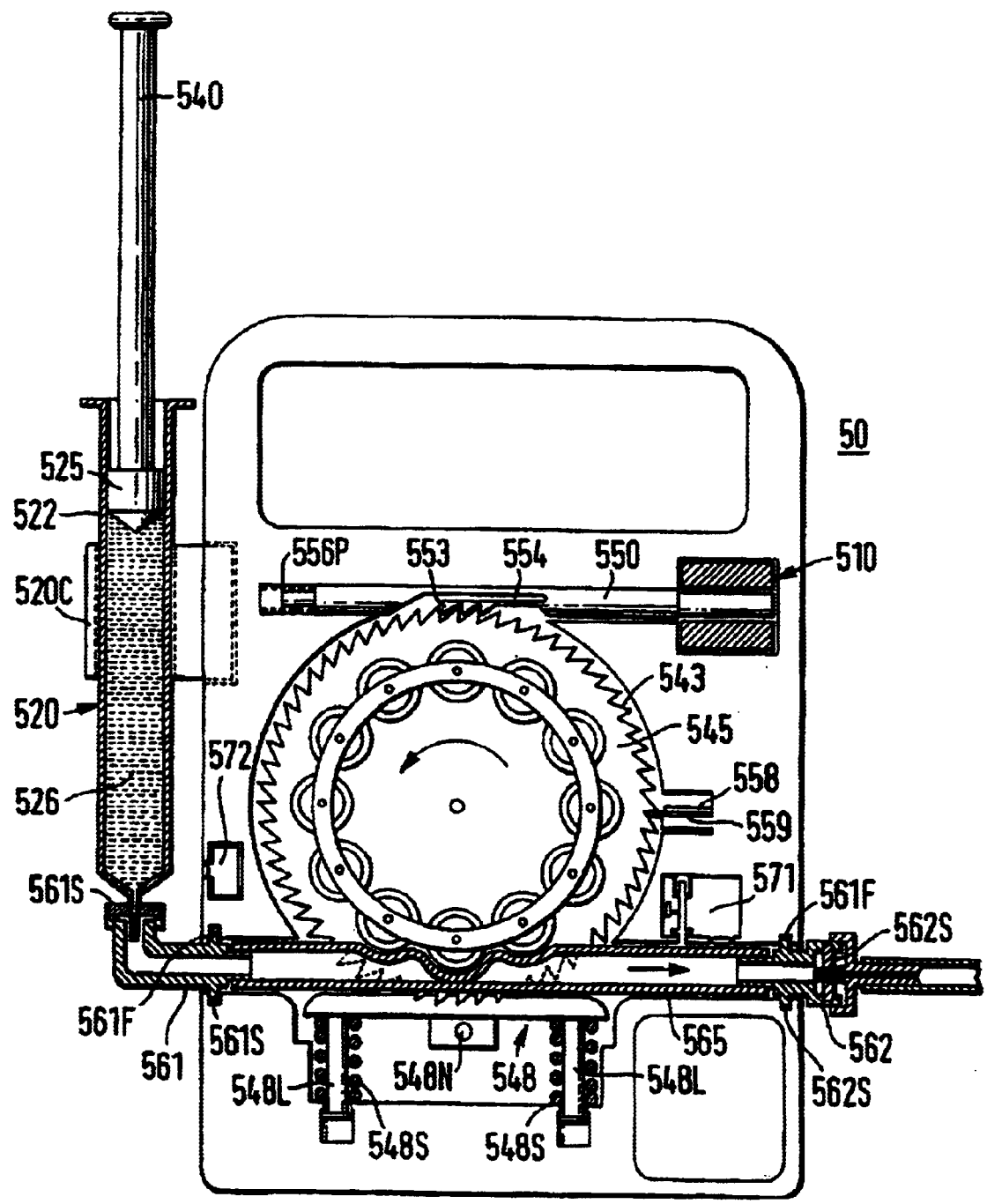
FIG. 8 is a part-sectional view of one peristaltic pump type drugs etc administration device.

Turning to FIG. 8, the arrangement of drive nut or wheel 545 with outer ratchet teeth 543 and pawl carrier 550 with pawl arm 554 and pawl 553 driven by solenoid 510 is similar to FIG. 7. Ratchet-latching and tooth-by-tooth movement sensing 558/9 are similar to FIG. 1. However, the drive nut or wheel 545 has an inner ring of freely rotatable rollers 546 and acts on a tube 565 against a pressure plate 548 shown spring-biassed at 548S about legs 548L, for a peristaltic pumping action. The spring-loaded pressure-plate 548 facilitates accommodation of different diameters of peristaltic tube 565. The flexible peristaltic tube 565 is shown disposed conveniently in a straight line path from an inlet fitting 561, shown as an elbow to an outlet fitting 562 shown straight, both of needle-less types and with pierceable septums 561S and 562S to appropriate connectors 561C, 562C. The drugs etc cart-ridge or syringe 520 is shown in a clip 520C alongside the peristaltic pump as such, and its contents 526 and seal piston 525 are simply drawn through the cartridge or syringe body part 522 by the peristaltic pumping action. A high/low pressure sensor for the peristaltic tube 565 is shown at 570, and a contents-used sensor at 571 for the cartridge 520. The inlet tube may be of or include means of a form-sustaining nature to prevent collapse under vaccuum, for which there may be an appropriate sensor.

It will be appreciated that simple application of gearing somewhat after the manner of FIG. 7, but applied to a rotatable carrier for the peristaltic rollers 546, say at a toothed or splined drive cog or shaft adds markedly to fineness and/or number of dosings in drugs etc or other materials supply systems, including, of course, part-tooth final drive movement.

The cartridge or syringe piston 525 is shown with an engaging piston-rod 540, which will usually be in relation to a re-usable syringe 525, i.e. rather than a pre-loaded cartridge (for operation of which no piston-rod would be required unless for some initialising procedure thus could be temporary and readily detachable). The intended incremental solenoid-driven ratchet operation should be evident from preceding description. Operation can readily involve a priming stage to fill the entire system, including delivery/administration tube with liquid, preferably as an operation separate and necessarily preceding switching the device on. User over-ride for extra dosing can readily be provided, much as before. A front cover, say of a cassette-style device, may be at least partially transparent, and readily removable for access, including fitting or re-fitting of intendedly (at least in medical applications) single-use peristaltic tubes 565, itself conveniently supplied complete with the connectors 561/2 to slide into position sideways (see flangings and slottings 561F, S and 562P, S) with the pressure plate 548 held down.

At least one of the flangings 561P, 562F may bear or incorporate coding to identify related tube bore diameter, perhaps also required pumping increment rate for a particular purpose, with automatic reading in the relevant slotting 561S, 562S (much as for cameras and photographic films). Preferably, such access is controlled by suitable means, such as knob 548N, which cannot be operated with the device in use, further preferably operating an alarm if any attempt is made to do so.

Figure 9:
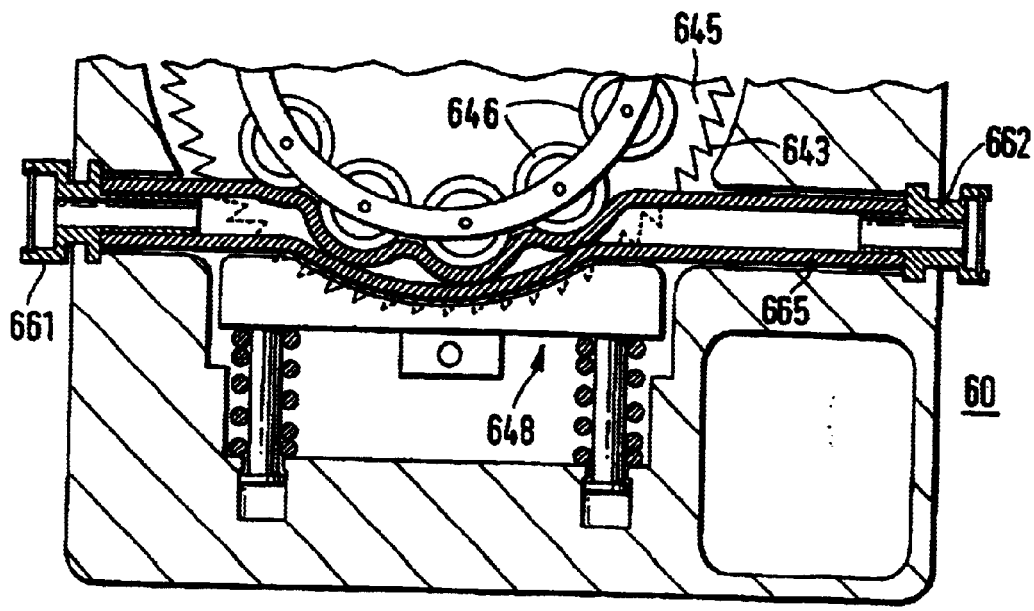
FIG. 9 is an incomplete view showing a variant peristaltic device.

FIG. 9 shows variations on FIG. 8 by way of a straight inlet fitting 661, and arcuate recessing 648R of its pressure plate 648 opposite to and concentrically with the toothed and rollered wheel 645. The recessing 648R increases the length of peristaltic tube that is squeezed by the rollers 646 in incremental administration action.

Figure 10:
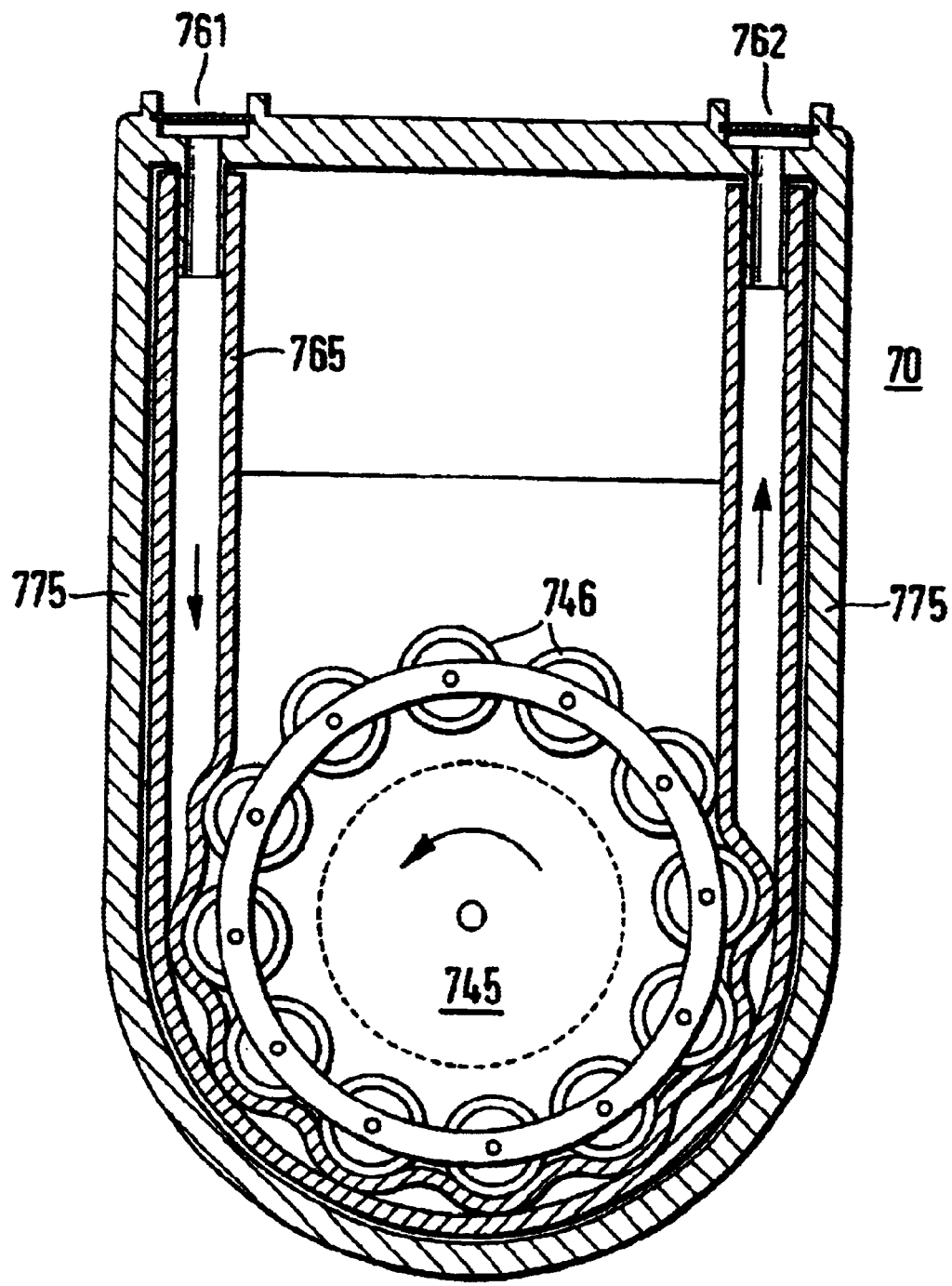
FIG. 10 shows a third peristaltic device.

Turning to peristaltic-action device 70 of FIG. 10, its toothed (not shown) and rollered wheel 745 is shown inside a U-shaped constraining wall 775 against which the peristaltic tube 765 is squeezed by the wheel rollers 746 for a full half-circle. The peristaltic tube 765 extends between inlet and exit formations or fittings 761, 762 in or at an end wall. Further front and back walls (not shown) can usefully complete a compact and convenient cassette-style materials flow/delivery device. It will be appreciated that the ratchet teeth of or for the wheel 765 can, at least in this embodiment, be at a stepping of lesser diameter than the rollers 746 (see dashed circle 743).

Figure 11:
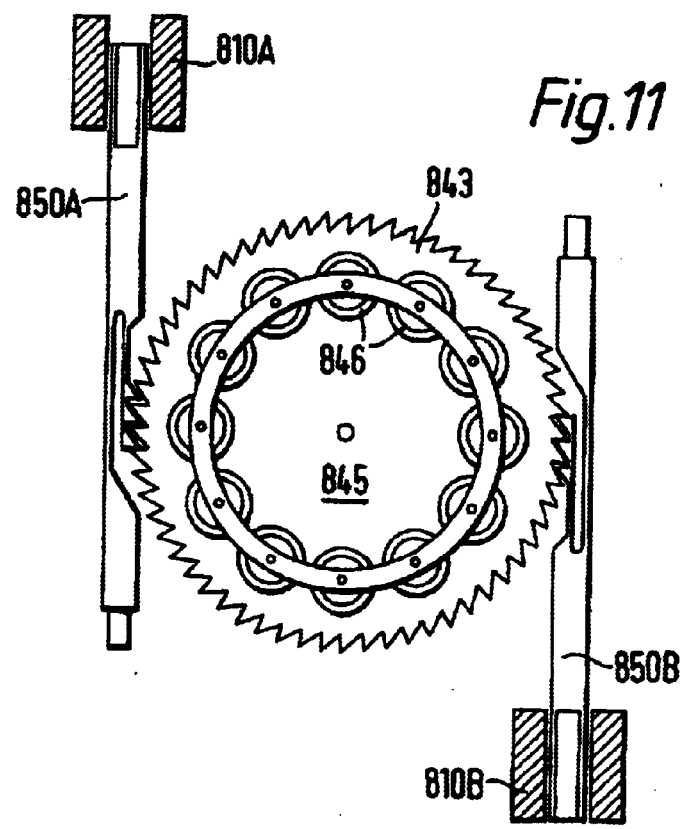
FIG. 11 shows variant two-solenoid-drive system.

At least in applying solenoid- and ratchet incremental drive embodiments of this invention as direct replacements for pumps, for whatever purpose(s), it can be useful and advantageous at least to approximate more closely to a continuous driving/delivery action. FIG. 11 shows this readily achieved by a particular form of dual solenoid/pawl drive provisions acting alternately on the same ratchet provision, see solenoids 810A, B with pawl carriers 850A, B acting tangentially on the same ring of ratchet teeth 843, further shown, conveniently (but not necessarily) acting in parallel directions at convenient diametrically opposite positions on a ratchet wheel 845 also shown (non-limitingly) as bearing peristaltic rollers 846. Damping could be applied to each solenoid and/or pawl-carrier action, e.g. at the end of the solenoid-driven pawl-carrier, whether by springs or hydraulics or pneumatics. Perhaps ideally, or at least sometimes advantageously, hydraulic/pneumatic damping action can be linked through a tube, say with flow either way subjected to appropriate restriction, conveniently by a valve, with a resulting affect on delivery, and possibility readily of counting solenoid pulses having a direct relationship to pumped volume(s).

Figure 12A:
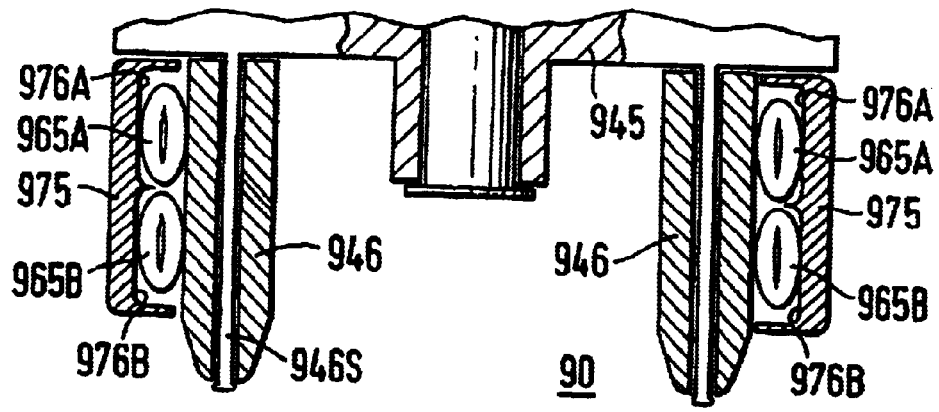
Figure 12B:
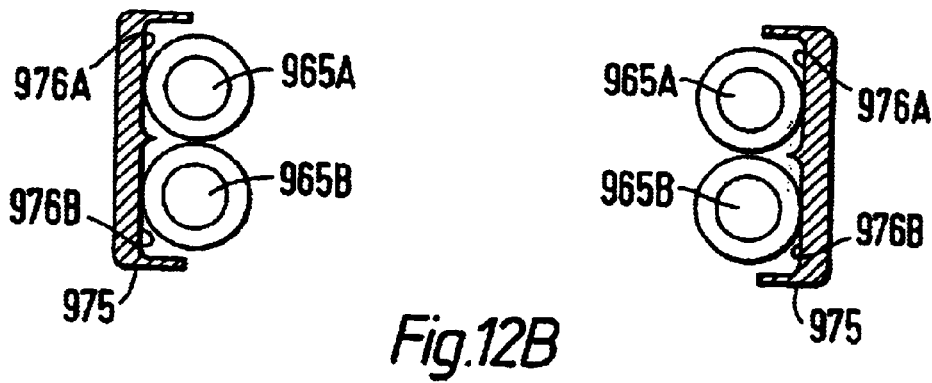
Figure 12C:
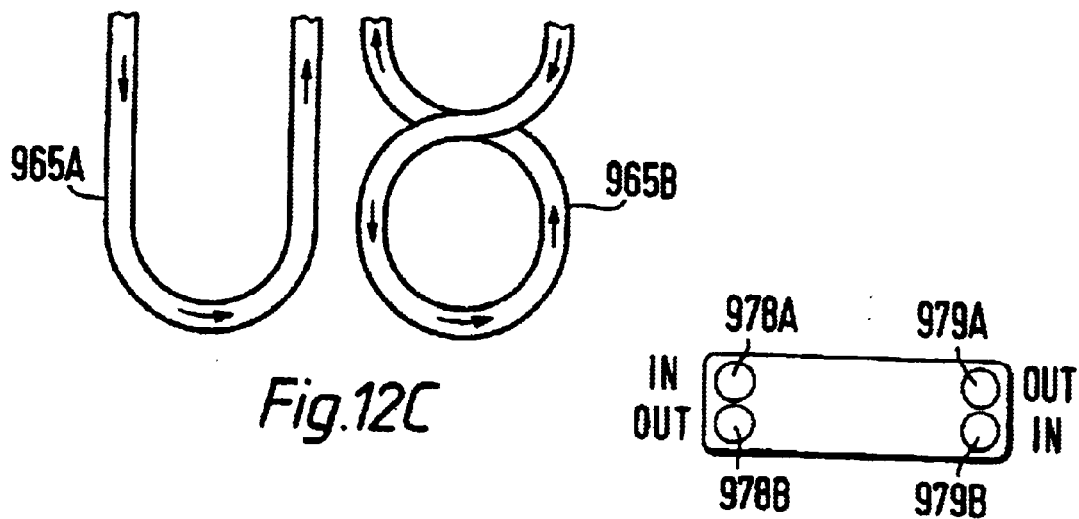
Figure 12D:
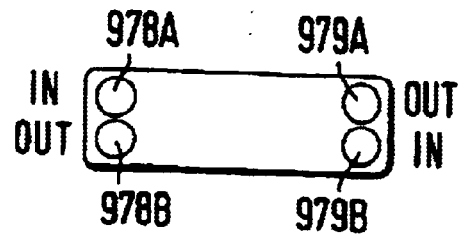

Turning to FIG. 12, another cassette-style peristaltic system/device 90, configured generally similarly to FIG. 10, is shown in outline with constraining wall 975 formed at 976A, B to locate two peristaltic tubes 965A, B side-by-side, FIGS. 12A and 12B being outline sections at and above its hub-mounted drive wheel 945, respectively. The ratchet-wheel 945 has rotation spindles 946S for peristaltic tube-squeezing rollers 946, each acting simultaneously on both of the tubes 965A, B. FIG. 12C shows peristaltic tube configurations separately, with tube 965A as in the embodiment of FIG. 10, but the tube 965B crossing above the position for the ratchet wheel 945, thereby allowing (see FIG. 12D) IN and OUT connections 978A, B and 978A, B at each side of the top 91 of the device 90 to source and destination in a fluid transfer system as used for immediately recycling type out-of-body treatment of blood.

What is claimed is:

1. Materials delivery device for controlling flow of material in administration thereof, comprising a dispenser body in which material to be dispensed is held and from which it is to be delivered;

means for administering material including parts movable relative to the dispenser body to dispense the material therefrom, solenoid means intermittently operable to provide drive force for incremental operation of the means for administering, and drive transmission means comprising a toothed pawl provided on a substantially linear carrier, and toothed actuator means, which is engageable by the toothed pawl and is drivable by the toothed pawl in a one-way non-returnable manner so as to move the means for administering incrementally, in which respect the substantially linear carrier of the toothed pawl is reciprocable in a substantially linear manner, being intermittently driven by the solenoid means in a first direction and being returned under spring-bias in an opposite direction, and the toothed pawl is provided on a deflectable portion of the linear carrier so as to disengage automatically from the toothed actuator means in one of the first or opposite directions.

2. Device according to claim 1, wherein driving of one-way non-returnable movement of the toothed actuator means by the toothed pawl is one tooth pitch each time.

3. Device according to claim 1, wherein said toothed actuator means has associated ratchet latching means preventing any backward movement beyond drive increments of its movement.

4. Device according to claim 3, wherein said ratchet latching means has associated signaling means.

5. Device according to claim 4, wherein the signaling means includes a piezoelectric device.

6. Device according to claim 3, wherein the ratchet latching means comprises a one-way deflecting tooth member.

7. Device according to claim 1, wherein said toothed actuator means includes a linear track of teeth.

8. Device according to claim 1, wherein the means for administering material is a piston assembly comprising a piston-rod driving a piston, said piston being sealingly disposed within the dispenser body and movable relative to the dispenser body to dispense the material therefrom, the solenoid means is intermittently operable to provide drive force for incremental operation of the piston-rod, and the drive transmission means comprises a toothed pawl provided on a substantially linear carrier, and toothed actuator means, which is engageable by the toothed pawl and is drivable by the toothed pawl in a one-way non-returnable manner so as to move the piston-rod incrementally.

9. Device according to claim 8, having energy storage-and-release provision associated with said piston and piston-rod to absorb and re-transmit drive stroke of said toothed actuator means by said toothed pawl and mitigate spurting of liquid said material.

10. Device according to claim 9, having electric switch means operative after energy release corresponding to full stroke piston movement.

11. Device according to claim 8, wherein driving of one-way non-returnable movement of the toothed actuator means by the toothed pawl is one tooth pitch each time.

12. Device according to claim 8, wherein said toothed actuator means has associated ratchet latching means preventing any backward movement beyond drive increments of its movement.

13. Device according to claim 12, wherein the ratchet latching means comprises a one-way deflecting tooth member.

14. Device according to claim 12, wherein said ratchet latching means has associated signaling means.

15. Device according to claim 14, wherein the signaling means includes a piezoelectric device.

16. Device according to claim 8, wherein said toothed actuator means includes a linear track of teeth.

17. Device according to claim 8, having means to connect with supply of medicament and with patient-entrant means to serve at least in parenteral administration.

18. Parenteral drug delivery device according to claim 17, having a portable carrier for all its parts including electric battery for power and accommodation for a pre-loaded medicament cartridge with its piston engageable for operation by piston-rod means associated with said toothed actuator means.

19. Device according to claim 18, wherein said carrier houses a cylindrical holder with the cartridge at a relatively forward position in the holder and the piston-rod relatively rearward in the holder alongside ratchet-type said drive transmission provisions.

20. Device according to claim 18, wherein the holder has means cooperating with a hollow delivery needle from the cartridge that is selectively exposable out of the holder and the carrier at least for its pointed end.

21. Device according to claim 20, wherein said needle has an angled medial bend or joint and is deflectable by said cooperating means to force its end out of the holder or extension thereof.

22. Device according to claim 21, wherein said cooperating forcing means is operable by a dedicated solenoid at the forward end of the holder or carrier.

23. Device according to claim 1, having means to connect with supply of medicament and with patient-entrant means to serve at least in parenteral administration.

24. Parenteral drug delivery device according to claim 23, having a portable carrier for all its parts including electric battery for power and accommodations for a pre-loaded medicament cartridge with its piston engageable for operation by piston-rod means associated with said toothed acutator means.

25. Device according to claim 24, wherein said carrier houses a cylindrical holder with the cartridge at a relatively forward position in the holder and the piston-rod relatively rearward in the holder alongside ratchet-type said drive transmission provisions.

26. Device according to claim 24, wherein the holder has means cooperating with a hollow delivery needle from the cartridge that is selectively exposable out of the holder and the carrier at least for its pointed end.

27. Device according to claim 26, wherein said needle has an angled medial bend or joint and is deflectable by said cooperating means to force its end out of the holder or extension thereof.

28. Device according to claim 27, wherein said cooperating forcing means is operable by a dedicated solenoid at the forward end of the holder or carrier.

* * * * *